(12) United States Patent
Ramakrishnan

(10) Patent No.: US 6,919,185 B2
(45) Date of Patent: Jul. 19, 2005

(54) REGULATION OF HUMAN TRANSKETOLASE-LIKE ENZYME

(75) Inventor: Shyam Ramakrishnan, Brighton, MA (US)

(73) Assignee: Bayer Aktiengesellschaft, Leverkusen (DE)

( * ) Notice: Subject to any disclaimer, the term of this patent is extended or adjusted under 35 U.S.C. 154(b) by 329 days.

(21) Appl. No.: 10/296,144

(22) PCT Filed: May 30, 2001

(86) PCT No.: PCT/EP01/06125

§ 371 (c)(1),
(2), (4) Date: Nov. 22, 2002

(87) PCT Pub. No.: WO01/92310

PCT Pub. Date: Dec. 6, 2001

(65) Prior Publication Data

US 2003/0113329 A1 Jun. 19, 2003

Related U.S. Application Data

(60) Provisional application No. 60/207,950, filed on May 31, 2000.

(51) Int. Cl.[7] .............................. C12Q 1/48; C12N 9/10; C12N 15/54
(52) U.S. Cl. .................. 435/15; 435/193; 536/23.2
(58) Field of Search .................. 435/15, 193; 536/23.2; 530/350

(56) References Cited

FOREIGN PATENT DOCUMENTS

| WO | WO 97/05253 | 2/1997 |
|---|---|---|
| WO | WO 01/12659 | 2/2001 |
| WO | WO 01/66752 | 9/2001 |

OTHER PUBLICATIONS

A_GeneSeq Data Base Acc#ABU52999 WO200112659 PD Feb. 22, 2001 Wiemann S. Alignment with SEQ ID NO: 2.*
Database EMBL 'Online!, "SEQ ID NO: 513 from patent WO 01 12659", Feb. 22, 2001, Database Accession No. AX086561, XP002185367.
Database EMBL 'Online!, "SEQ ID NO: 512 from patent WO 01 12659", Mar. 6, 2001, Database Accession No. AX086560, XP002185368.
Database EMBL 'Online!, "SEQ ID NO: 511 from patent WO 01 12659", Mar. 9, 2001, Database Accession No. AX086559, XP002184772.
Database EMBL 'Online!, Mar. 3, 2000, retrieved from EBI Database Accession No. AC015457, XP002184732, *Homo sapiens* chromosome 4, clone RP11–218F10, Nucleotides: 38520–42060.
Database EMBL 'Online!, "*H. sapiens* mRNA for transketolase–like protein", Database Accession No. X91817, XP002185233 (Mar. 1996).
Coy J. F., et al., "Molecular Cloning of Tissue–Specific Transcripts of a Transketolase–Related Gene: Implications for the Evolution of New Vertebrate enes", Genomics, Academic Press, San Diego, US, Mar. 15, 1996, vol. 32, No. 3, pp 309–316, XP000616489.
McCool B. A., et al., "Cloning of Human Transketolase CDNAS and Comparison of the Nucleotide Sequence of the Coding Region in Wernicke–Korsakoff and Non–Wernicke–Korsakoff Individuals", Journal Of Biological Chemistry, American Society of Biological Chemists, Baltimore, MD, Jan. 15, 1993, vol. 268, No. 2, pp 1397–1404, XP002023965.

* cited by examiner

*Primary Examiner*—Rebecca Prouty
(74) *Attorney, Agent, or Firm*—Banner & Witcoff, Ltd.

(57) ABSTRACT

Reagents which regulate human transketolase-like enzyme and reagents which bind to human transketolase-like enzyme gene products can play a role in preventing, ameliorating, or correcting dysfunctions or diseases including, but not limited to, cancer, anemia, and end-stage renal disease, including sensory periphery neuropathy associated with uremia.

3 Claims, 9 Drawing Sheets

Fig. 1

TTTAACGTGAAGTTAAGGTAAGAATTATTGCTCAAGAAACCAAGAGGTTT
AACATCGCAATATGGGAAGGTATGATATATTATCATTGTGTTTTTTTTAA
TTGTTGTTTTATTGATGACAAACCATAACCTTGGCCTGCTAGAAGAGTTC
AATGGCACAAATTTAGTTTTTTTTTGTTTTAGACGGAGTCTCGCTCTGTCT
CCCAGGCTGGAGTGCAGTGGCACAATCTGGGCTCACTGCAAGCTCCACCT
CCCAGGTTCACGCCATTCTCCTGCCTCAGCCTCCCGAGTAGCTGGGACTA
CAGGTGCCCATCACCACGCCCAGCTAATTTTTTTGTATTTTTAGTAGACA
CGGGGTTTCACCGTGTTAGCCAGGATGGTCTCGAACTCCTGACCTTGTGA
TCCGCCTGCCTCGGCCTCCCAAAGTGCTGGGATTACAGGTGTGAGCCACA
GCACCCGGCCCACAAATTTAGTTTTTTAAAGTAAGTAACTTTGTCTTAAA
AATGATTTGTAGTAATAGTCATTAAAAGATAAACTGAGGCACATTAAAAT
ATTAAAGCATTTATTTGACCATTCAGTGATTCATGAATCTGGTAGCTCCT
GATAAAGGAGCCAAGGAGAAGGCTTTTATAGGGTGAATTTGGAAGCAAAG
GAAAGATATTTGATTGGTTAAAGTGGAGTACTAGACTTATTTGGGTCATC
CCAGTGGAAAGTCCCCAGTTAGAAGTTAGCTGGCAGTTTCTGATTGATTA
AGCTTAAATTTCCTTTTTATCATTTACACTGATTTGGGTTTCCTTTCCTT
AGGTAGGAACTCATGGAGCTGAAGCTACCTCAGCCTACTGGCCTTCTAAT
TATTTCAACACAGAAATAGTACTTTACGGCACACTGGAGTTGCAATTCTA
TTCTGCAATTGGGTGGTTTCAGATTTGTTCTTCCTATAAATTTTGGTCAA
ATTAGTCATTGCATTTCTTTCTATAAGTCTGAGATTCAGATATTTGGTTG
CTCTGAGAAAGTCTCTGTTGAGATAGCATTGCCATACTGGTCAGATTGAA
AGTGACTTTGTATCCTTTCTATTAATGTTCTGATATGAAAGAGTGATGAC
TCGGATATAGTGTTAATGCATTAAAAAAGCACAGCCTGACAAATCGCTTC
CTATAATACACAGAAAAATGTCTAGTCTTGAATTTATAACACAGGGAAAG
GTAAAAAATTTAATTATGCTTCCTAATGTTGAACATGCACGTGACAAAGT
AAATACTAAAAATCCATTCAGCTGGGCGTGGACAGGGAGAGGGAACGGTG
CACATCAGAGGGTGCAGGCTACTCCAACGTTTCCGTTTCCTCAGTCTCGC
GGGAAGCTCCGTTGTGGGCGCCCCGGCTGGTGGCTGAGCTCAGGCCTTCA
GGCAGAGGGGAGGCGAGGGCGGGGCGGTCACGTGAGAGCACTGCCGCGGT
GGGTTGTGGGGGTGCTGCGGCGCCGTTTGCTTTGCCAAACCGACAAAAGA
GAGATGATGGCCAACGACGCCAAGCCCGACGTGAAGACCGTGCAGGTGCT
GCGGGACACAGCCAACCGCCTGCGGATCCATTCCATCAGGGCCACGTGTG
CCTCTGGTTCTGGCCAGCTCACGTCGTGCTGCAGTGCAGCGGAGGTCGTG
TCTGTCCTCTTCTTCCACACGATGAAGTATAAACAGACAGACCCAGAACA

Fig. 1(cont'd)

```
CCCGGACAACGACCGGTTCATCCTCTCCAGGGGACATGCTGCTCCTATCC
TCTATGCTGCTTGGGTGGAGGTGGGTGACATCAGTGAATCTGACTTGCTG
AACCTGAGGAAACTTCACAGCGACTTGGAGAGACACCCTACCCCCGATT
GCCGTTTGTTGACGTGGCAACAGGGTCCCTAGGTCAGGGATTAGGTACTG
CATGTGGAATGGCTTATACTGGCAAGTACCTTGACAAGGCCAGCTACCGG
GTGTTCTGCCTTATGGGAGATGGCGAATCCTCAGAAGGCTCTGTGTGGGA
GGCTTTTGCTTTTGCCTCCCACTACAACTTGGACAATCTCGTGGCGGTCT
TCGACGTGAACCGCTTGGGACAAAGTGGCCCTGCACCCCTTGAGCATGGC
GCAGACATCTACCAGAATTGCTGTGAAGCCTTTGGATGGAATACTTACTT
AGTGGATGGCCATGATGTGGAGGCCTTGTGCCAAGCATTTTGGCAAGCAA
GTCAAGTGAAGAACAAGCCTACTGCTATAGTTGCCAAGACCTTCAAAGGT
CGGGGTATTCCAAATATTGAGGATGCAGAAAATTGGCATGGAAAGCCAGT
GCCAAAAGAAAGAGCAGATGCAATTGTCAAATTAATTGAGAGTCAGATAC
AGACCAATGAGAATCTCATACCAAAATCGCCTGTGGAAGACTCACCTCAA
ATAAGCATCACAGATATAAAAATGACCTCCCCACCTGCTTACAAAGTTGG
TGACAAGATAGCTACTCAGAAAACATATGGTTTGGCTCTGGCTAAACTGG
GCCGTGCAAATGAAAGAGTTATTGTTCTGAGTGGTGACACGATGAACTCC
ACCTTTTCTGAGATATTCAGGAAAGAACACCCTGAGCGTTTCATAGAGTG
TATTATTGCTGAACAAAACATGGTAAGTGTGGCACTAGGCTGTGCTACAC
GTGGTCGAACCATTGCTTTTGCTGGTGCTTTTGCTGCCTTTTTTACTAGA
GCATTCGATCAGCTCCGAATGGGAGCCATTTCTCAAGCCAATATCAACCT
TATTGGTTCCCACTGTGGGGTATCCACTGGAGAAGATGGAGTCTCCCAGA
TGGCCCTGGACGATCTAGCCATGTTCCGAAGCATTCCCAATTGTACTGTT
TTCTATCCAAGTGATGCCATCTCGACAGAGCATGCTATTTATCTAGCCGC
CAATACCAAGGGAATGTGCTTCATTCGAACCAGCCAACCAGAAACTGCAG
TTATTTATACCCCACAAGAAAATTTTGAGATTGGCCAGGCCAAGGTGGTC
CGCCACGGTGTCAATGATAAAGTCACAGTAATTGGAGCTGGAGTTACTCT
CCATGAAGCCTTAGAAGCTGCTGACCATCTTTCTCAACAAGGTATTTCTG
TCCGTGTCATCGACCCATTTACCATTAAACCCCTGGATGCCGCCACCATC
ATCTCCAGTGCAAAAGCCACAGGCGGCCGAGTTATCACAGTGGAGGATCA
CTACAGGGAAGGTGGCATTGGAGAAGCTGTTTGTGCAGCTGTCTCCAGGG
AGCCTGATATCCTTGTTCATCAACTGGCAGTGTCAGGAGTGCCTCAACGT
GGGAAAACTAGTGAATTGCTGGATATGTTTGGAATCAGTACCAGACACAT
TATAGCAGCCGTAACACTTACTTTAATGAAGTAAACTAGGCTTATTTC
TAAAAAGTCAAGTCTATTGGCTTTGGCCCAAAAGCACTGGTATCTTTGTA
TTAAATTCATGTTTATTGTCACAAAACCATTATTTATACCTATACAGTTG
```

Fig. 1(cont'd)

TACTGTTTCTTTTAAAGCAAAGCCATTTAACATCTTTCTTCA

Fig. 2

MANDAKPDVKTVQVLRDTANRLRIHSIRATCKSGSGQLTSCCSAAEVVSVLFFHTMKYKQ
TDPEHPDNDRFILSRGHAAPILYAAWVEVGDISESDLLNLRKLHSDLERHPTPRLPFVDV
ATGSLGQGLGTACGMAYTGKYLDKASYRVFCLMGDGESSRGSVWEAFAFASHYNLDNLVA
VFDVNRLGQSGPAPLEHGADIYQNCCEAFGWNTYLVDGHDVEALCQAFWQASQVKNKPTA
IVAKTFKGRGIPNIEDAENWHGKPVPKERADAIVKLIESQIQTNENLIPKSPVEDSPQIS
ITDIKMTSPPAYKVGDKIATQRTYGLALAKLGRANERVIVLSGDTMNSTFSEIFRKEHPE
RFIECIIAEQNMVSVALGCATRGRTIAFAGAFAAFPTRAFDQLRMGAISQANINLIGSHC
GVSTGEDGVSQMALEDLAMFRSIPNCTVFYPSDAISTEHAIYLAANTKGMCFIRTSQPET
AVIYTPQENFEIGQAKVVREGVNDKVTVIGAGVTLHEALEAADHLSQQGISVRVIDPFTI
KPLDAATIISSAKATGGRVITVEDHYREGGIGEAVCAAVSREPDILVHQLAVSGVPQRGK
TSELLDMFGISTRHIIAAVTLTLMK

Fig. 3 megyhkpdqq klqalkdtan rlrissiqat taagsghpts ccsaaeimav lffhtmryka
ldprnphndr fvlskghaap ilyavwaeag flpeaellnl rkissdldgh pvpkqaftdv
atgslgqglg aacgmaytgk yfdkasyrvy cmlgdgevse gsvweamafa giykldnlva
ifdinrlgqs dpaplqhqvd iyqkrceafg whtiivdghs veelckafgq akhqptaila
ktfkgrgitg iedkeawhgk plpknmaeqi iqeiysqvqs kkkilatppq edapsvdian
inmptppsyk vgdkiatrka yglalaklgh asdriialdg dtknstfsel fkkehpdrfi
ecyiaeqnmv siavgcatrd rtvpfcstfa afftrafdqi rmaaisesni nlcgshcgvs
igedgpsqma ledlamfrsv pmstvfypsd gvatekavel aantkgicfi rtsrpenaii
ysnnedfqvg qakvvlkskd dqvtvigagv tlhealaaae slkkdkisir vldpftikpl
drklildsar atkgriltve dhyyeggige avsaavvgep gvtvtrlavs qvprsgkpae
llkmfgidkd aivqavkglv tkg

Fig. 4

PHNDRFVLSKGHAAPILYAVWAEAGFLPEAELLNLRKISSDLDGHPVPKQAFTDVATGSL

Fig. 5

MSKARAEKDTLWAGAGVGAADAVKATRQTVDAWLVSHATSAGNDVVSSTSPTHANGQTSSSRGGSGATTP
VRKISAHEPERGGLLKPIVNTIDGTPTFLSIGPPMDNGSVGGSCSNLQNVGGVVAGQYQYNHQQHHHNHA
HLHHSQHSHYQAGGAVGSSSLGSTGGASGAGGAPSLGGSGGAGNGHQYPYYHCHQRPQRLSRNELKQLDE
KELIPELVKDICNELEVRTLCHKILQNVSILDNADRGSLFLVQGRCNGPDGLKKCLVSKLFDVCPRSTVE
EMEQQDEVRVAWGTGIAGHVAESGEPVNIPDAYQDERFNCEIDSLTGYRTKALLCMPIKDSSGDVIGVAQ
VINKMNGECFSEIDEKVFSSYLQFCGIGLRNAQLYEKSQLEIKRNQVLLDLARMIPEEQSTIEHMVPRIL
THMQSLIQCQRVQILLVHEADKGSFSRVFDFEANDLSEEEATSRTSPYESRFPINIGITGHVATTGETVN
VPNAYEDDRFDASVDENSCFKHRSILCMAIRNSLGQIIGVIQLINKFNELDPTKNDENFVEAPAIPCGHG
IHNTHMYEKAIVAMAKQSVTLEVLSYHASATMDEAHRLRKQKQQQQAVGLRQAPLSLPPRKKLQRRLRVP
SAVHFRLHDFKFDDIHPEDDDTLKACLRMFLDLDFVERFHIDYEVLCRWLLSVKKNYRNVTYHNWRHAFN
VAQMMPAILTTTQWWKIPGEIECLALIIGCLCHDLDHRGTNNSFQIKASSPLAQLYSTSTMEHHHFDQCL
MILNSPGNQILANLSSDDYCRVIRVLEDAILSTDLAVYFKKRGPPLESVSQPTSYWVAEEPRALLRAMSM
TVCDLSAITKPWBIEKRVADLVSSEFFEQGDMEKQELNITPIDIMNREKEDELPMMQVNFIDSICLPIYE
APATLSDKLEPLVEGVRDNRGHWIDLADVVKTKTSQDQEPEEEQQQQNVISNGDCKAMSDDDVAASEAEV
AVDSPSEKASVNGSNVANNSSNTNKKIAVASHPTSTQPSDDDNDVDADADDVDEQAAEENGHDAEVDEAS
CRSNSTCSSSTASSCLSTPPPTGEDDSTPVSPLKTLQAKLVAANLNALQRQTSNQAQTQKQRCKSCDHSR
SGLQVRKTSSLRGAQELDLDSKTRNGTHAALCKSTPVINNHSHHHNHSHSHNHNHHHHHHHSHHNHSQH
GIGIGSASIGGSGLISLTTPLLAMDSDRIPKIVGKIGNLDGLPFANGIGGPQNGHGLPFGSYQHFHTHEQH
HHHLLARRHSETNSNGATAMAVEK

Fig. 6

<u>ATG</u>ATGGCCAACGACGCCAAGCCCGACGTGAAGACCGTGCAGGTGCT
GCGGGACACAGCCAACCGCCTGCGGATCCATTCCATCAGGGCCACGTGTG
CCTCTGGTTCTGGCCAGCTCACGTCGTGCTGCAGTGCAGCGGAGGTCGTG
TCTGTCCTCTTCTTCCACACGATGAAGTATAAACAGACAGACCCAGAACA
CCCGGACAACGACCGGTTCATCCTCTCCAGGGGACATGCTGCTCCTATCC
TCTATGCTGCTTGGGTGGAGGTGGGTGACATCAGTGAATCTGACTTGCTG
AACCTGAGGAAACTTCACAGCGACTTGGAGAGACACCCTACCCCCGATT
GCCGTTTGTTGACGTGGCAACAGGGTCCCTAGGTCAGGGATTAGGTACTG
CATGTGGAATGGCTTATACTGGCAAGTACCTTGACAAGGCCAGCTACCGG
GTGTTCTGCCTTATGGGAGATGGCGAATCCTCAGAAGGCTCTGTGTGGGA
GGCTTTTGCTTTTGCCTCCCACTACAACTTGGACAATCTCGTGGCGGTCT
TCGACGTGAACCGCTTGGGACAAAGTGGCCCTGCACCCCTTGAGCATGGC
GCAGACATCTACCAGAATTGCTGTGAAGCCTTTGGATGGAATACTTACTT

Fig. 6(cont'd)

```
AGTGGATGGCCATGATGTGGAGGCCTTGTGCCAAGCATTTTGGCAAGCAA
GTCAAGTGAAGAACAAGCCTACTGCTATAGTTGCCAAGACCTTCAAAGGT
CGGGGTATTCCAAATATTGAGGATGCAGAAAATTGGCATGGAAAGCCAGT
GCCAAAAGAAAGAGCAGATGCAATTGTCAAATTAATTGAGAGTCAGATAC
AGACCAATGAGAATCTCATACCAAAATCGCCTGTGGAAGACTCACCTCAA
ATAAGCATCACAGATATAAAAATGACCTCCCCACCTGCTTACAAAGTTGG
TGACAAGATAGCTACTCAGAAACATATGGTTTGGCTCTGGCTAAACTGG
GCCGTGCAAATGAAAGAGTTATTGTTCTGAGTGGTGACACGATGAACTCC
ACCTTTTCTGAGATATTCAGGAAAGAACACCCTGAGCGTTTCATAGAGTG
TATTATTGCTGAACAAAACATGGTAAGTGTGGCACTAGGCTGTGCTACAC
GTGGTCGAACCATTGCTTTTGCTGGTGCTTTTGCTGCCTTTTTTACTAGA
GCATTCGATCAGCTCCGAATGGGAGCCATTTCTCAAGCCAATATCAACCT
TATTGGTTCCCACTGTGGGGTATCCACTGGAGAAGATGGAGTCTCCAGA
TGGCCCTGGAGGATCTAGCCATGTTCCGAAGCATTCCCAATTGTACTGTT
TTCTATCCAAGTGATGCCATCTCGACAGAGCATGCTATTTATCTAGCCGC
CAATACCAAGGGAATGTGCTTCATTCGAACCAGCCAACCAGAAACTGCAG
TTATTTATACCCCACAAGAAAATTTTGAGATTGGCCAGGCCAAGGTGGTC
CGCCACGGTGTCAATGATAAAGTCACAGTAATTGGAGCTGGAGTTACTCT
CCATGAAGCCTTAGAAGCTGCTGACCATCTTTCTCAACAAGGTATTTCTG
TCCGTGTCATCGACCCATTTACCATTAAACCCTGGATGCCGCCACCATC
ATCTCCAGTGCAAAAGCCACAGGCGGCCGAGTTATCACAGTGGAGGATCA
CTACAGGGAAGGTGGCATTGGAGAAGCTGTTTGTGCAGCTGTCTCCAGGG
AGCCTGATATCCTTGTTCATCAACTGGCAGTGTCAGGAGTGCCTCAACGT
GGGAAAACTAGTGAATTGCTGGATATGTTTGGAATCAGTACCAGACACAT
TATAGCAGCCGTAACACTTACTTTAATGAAGTAA
```

Fig. 7

BLASTP - alignment of 112 against swissnew|P40142|TKT_MOUSE
TRANSKETOLASE (EC 2.2.1.1) (TK) (P68).//:swiss|P40142|TKT_MOUSE
TRANSKETOLASE (EC 2.2.1.1) (TK) (P68).//:trembl|U05809|MM05809_1 product:
"transketolase"; Mus musculus LAF1 transketolase mRNA, complete cds.
//:gp|U05809|452486 product: "transketolase"; Mus musculus LAF1
transketolase mRNA, complete cds.
This hit is scoring at : 0.0 (expectation value)
Alignment length (overlap) : 614
Identities : 67 %
Scoring matrix : BLOSUM62 (used to infer consensus pattern)
Database searched : nrdb Q:      6  KPDVKTVQVLRDTANRLRIHSIRATCASGSGQLTSCCSAAEVVSVLFFHTMKYKQTDPEH
           KPD ::Q L:DTANRLRI SI:AT A:GSG  TSCCSAAE:::VLFFHTM:YK..DP.:
H:      6  KPDQQKLQALKDTANRLRISSIQATTAAGSGHPTSCCSAAEIMAVLFFHTMRYKALDPRN PDNDRFILSRGHAAPILYAAWVEVGDISESDLLNLRKLHSDLERHPTPRLPFVDVATGSL
           P.NDRF:LS:GHAAPILYA.W.E.G :.E::LLNLRK:.SDL: HP.P: .P.DVATGSL
           PHNDRFVLSKGHAAPILYAVWAEAGFLPEAELLNLRKISSDLDGHPVPKQAFTDVATGSL GQGLGTACGMAYTGKYLDKASYRVFCLMGDGESSEGSVWEAFAFASHYNLDNLVAVFDVN
           GQGLG.ACGMAYTGKY.DKASYRV:C::GDGE SEGSVWEA.APA. Y.LDNLVA:FD:N
           GQGLGAACGMAYTGKYPDKASYRVYCMLGDGEVSEGSVWEAMAFAGIYKLDNLVAIFDIN RLGQSGPAPLEHGADIYQNCCEAFGWNTYLVDGHDVEALCQAFWQASQVKNKPTAIVAKT
           RLGQS.PAPL:H .DIYQ. CEAFGW:T.:VDGH.VE.LC:AP QA    K::PTAI:AKT
           RLGQSDPAPLQHQVDIYQKRCEAFGWHTIIVDGHSVEELCKAFGQA---KHQPTAIIAKT FKGRGIPNIEDAENWHGKPVPKERADAIVKLIESQIQTNENLIPKSPVEDSPQISITDIK
           FKGRGI..IED.E WHGKP:PK..A:.I:: I SQ:Q:.:..:...P ED:P.:.I.:I:
           FKGRGITGIEDKEAWHGKPLPKNMAEQIIQEIYSQVQSKKKILATPPQEDAPSVDIANIR

MTSPPAYKVGDKIATQKTYGLALAKLGRANERVIVLSGDTMNSTFSEIFRKEHPERFIEC

Fig. 7(cont'd)

```
M..:PP:YKVGDKIAT:K.YGLALAKLG.A::R:I.L.GDT.NSTFSE:F:KEHP:RFIEC
MPTPPSYKVGDKIATRKAYGLALAKLGHASDRIIALDGDTKNSTFSELFKKEHPDRFIEC

IIAEQNMVSVALGCATRGRTIAFAGAFAAPFTRAFDQLRMGAISQANINLIGSHCGVSTG
.IAEQNMVS:A:GCATR.RT:.F...PAAPFTRAFDQ:RM.AIS::NINL.GSHCGVS.G
YIAEQNMVSIAVGCATRDRTVPFCSTFAAPFTRAFDQIRMAAISESNINLCGSHCGVSIG

EDGVSQMALEDLAMFRSIPNCTVFYPSDAISTEHAIYLAANTKGMCFIRTSQPETAVIYT
EDG SQMALEDLAMFRS:P .TVFYPSD.::TE.A: LAANTKG:CFIRTS:PE.A:IY:
EDGPSQMALEDLAMFRSVPMSTVFYPSDGVATEKAVELAANTKGICFIRTSRPENAIIYS

PQENFEIGQAKVVRHGVNDKVTVIGAGVTLHEALEAADHLSQQGISVRVIDPFTIKPLDA
.E:F::GQAKVV .. :D:VTVIGAGVTLHEAL.AA:.L.:. IS:RV:DPFTIKPLD.
NNEDPQVGQAKVVLKSKDDQVTVIGAGVTLHEALAAAESLKKDKISIRVLDPFTIKPLDR

ATIISSAKATGGRVITVEDHYREGGIGEAVCAAVSREPDILVHQLAVSGVPQRGKTSELL
..I:.SA:AT GR::TVEDHY EGGIGEAV.AAV EP.:.V :LAVS VP:.GK.:ELL
KLILDSARATKGRILTVEDHYYEGGIGEAVSAAVVGEPGVTVTRLAVSQVPRSGKPAELL

DMFGISTRHIIAAV      619
.MFGI.. I:.AV
KMFGIDKDAIVQAV      616
```

Fig. 8

The alignment below shows contains the pattern for transketolase 1:

R-x(3)-[LIVMTA]-[DENQSTHKF]-x(5,6)-[GSN]-G-H-[PLIVMF]-[GSTA]-x(2)-[LIMC]-[GS].

The histidine in this sequence is missing, and this histidine residue (italics) appears to function in proton transfer during catalysis.

```
Q:    6 KPDVKTVQVLRDTANRLRIHSIRATCASGSGQLTSCCSAAEVVSVLFFHTMKYKQTDPEH
        KPD :.:Q.L:DTANRLRI.SI:AT.A:GSG. TSCCSAAE:::VLFFHTM:YK..DP.:
H:    6 KPDQQKLQALKDTANRLRISSIQATTAAGSGHPTSCCSAAEIMAVLFFHTMRYKALDPRN
```

Fig. 9

Alignment showing Histidine110 (human enzyme co-ordinate, bold) and a yeast Histidine PDNDRPILSRGHAAPILYAAWVEVGDISESDLLNLRKLHSDLERHPTPRLPFVDVATGSL
P.NDRP:LS:GHAAPILYA.W.E.G :.E::LLNLRK:.SDL: HP.P: .P.DVATGSL
PHNDRFVLSKGHAAPILYAVWAEAGPLPEAELLNLRKISSDLDGHPVPKQAPTDVATGSL MANDAKPDVKTVQVLRDTANRLRIHSIRATCASGSGQLTSCCSAAEVVSVLFFHTMKYK
QTDPEHPDNDRPILSRGHAAPILYAAWVEVGDISESDLLNLRKLHSDLERHPTPRLPFV
DVATGSLGQGLGTACGMAYTGKYLDKASYRVFCLMGDGESSEGSVWEAPAPASHYNLDN
LVAVFDVNRLGQSGPAPLEHGADIYQNCCEAFGWNTYLVDGHDVEALCQAPWQASQVKN
KPTAIVAKTFKGRGIPNIEDAENWHGKPVPKERADAIVKLIESQIQTNENLIPKSPVED
SPQISITDIKMTSPPAYKVGDKIATQKTYGLALAKLGRANERVIVLSGDTMNSTFSEIP
RKEHPERPIECIIAEQNMVSVALGCATRGRTIAFAGAPAAFFTRAFDQLRMGAISQANI
NLIGSHCGVSTGEDGVSQMALEDLAMFRSIPNCTVFYPSDAISTEHAIYLAANTKGMCF
IRTSQPETAVIYTPQENPEIGQAKVVRHGVNDKVTVIGAGVTLHEALEAADHLSQQGIS
VRVIDPFTIKPLDAATIISSAKATGGRVITVEDHYREGGIGEAVCAAVSREPDILVHQL
AVSGVPQRGKTSELLDMFGISTRHIIAAVTLTLMK Transketolase region from residue 19 to 268 (bold and underlined)
Transketolase region from residue 310 to 615 (bold)
ATP_GTP_A region from residue 594 to 602. ATP/GTP binding region (italics)

REGULATION OF HUMAN TRANSKETOLASE-LIKE ENZYME

This application is the 371 national stage of PCT application PCT/EP01/06125 filed May 30, 2001, which was published in English under PCT Article 21(2) on Dec. 6, 2001, which claims the benefit of U.S. provisional application Ser. No. 60/207,950 filed May 31, 2000. These applications are incorporated herein by reference in their entireties.

TECHNICAL FIELD OF THE INVENTION

The invention relates to the regulation of a human transketolase-like enzyme.

BACKGROUND OF THE INVENTION

Transketolase contains $Mg^{++}$ and a tightly bound thiamin pyrophosphate and transfers a glycoaldehyde group from D-xylulose 5-phosphate to D-ribose 5-phosphate to form the seven-carbon sugar phosphate D-sedoheptulose 7-phosphate and D-glyceraldehyde 3-phosphate, which is an intermediate of glycolysis. See Lehninger, BIOCHEMISTRY, 2d ed., at pages 468–49 (1975). Genes which code for transketolase have been isolated and described from *Mus musculus* (Schimmer et al., *J. Biol. Chem.* 271, 4993–98, 1996), from *Saccharomyces cerevisiae* (Flechter et al., Biochemistry 31, 1892–96, 1993; Sundstrom et al., *J. Biol. Chem.* 268, 24346–52, 1993; Schaff-Gerstenschlager et al., *Eur. J. Biochem.* 217, 487–92, 1993), from *Hansenula polymorpha* (Janowicz et al., *Nucl. Acids Res.* 13, 3043–62, 1985), from human erythrocytes (Abedinia et al., *Biochem. Biophys. Res. Commun.* 183, 1159–66, 1992; McCool et al., *J. Biol. Chem.* 268, 1397–404, 1993), from *Rhodobacter sphaeroides* (Chen et al., *J. Biol. Chem.* 266, 20447–52, 1992) and from *Escherichia coli* (Sprenger, *Biochem. Biophys. Acta* 1216, 307–10, 1992; Tida et al., *J. Bacteriol.* 175, 5375–83, 1993). Two transketolase isoforms have been described in plant tissues (Murphy and Walker, *Planta* 155, 316–20, 1982). Because of the importance of this enzyme in a variety of metabolic pathways, there is a need in the art to identify additional human transketolase-like enzymes which can be regulated to provide therapeutic effects.

SUMMARY OF THE INVENTION

It is an object of the invention to provide reagents and methods of regulating a human transketolase-like enzyme. This and other objects of the invention are provided by one or more of the embodiments described below.

One embodiment of the invention is a transketolase-like enzyme polypeptide comprising an amino acid sequence selected from the group consisting of:

amino acid sequences which are at least about 70% identical to the amino acid sequence shown in SEQ ID NO: 2; and the amino acid sequence shown in SEQ ID NO: 2.

Yet another embodiment of the invention is a method of screening for agents which decrease extracellular matrix degradation. A test compound is contacted with a transketolase-like enzyme polypeptide comprising an amino acid sequence selected from the group consisting of:

amino acid sequences which are at least about 70% identical to the amino acid sequence shown in SEQ ID NO: 2; and the amino acid sequence shown in SEQ ID NO: 2.

Binding between the test compound and the transketolase-like enzyme polypeptide is detected. A test compound which binds to the transketolase-like enzyme polypeptide is thereby identified as a potential agent for decreasing extracellular matrix degradation. The agent can work by decreasing the activity of the transketolase-like enzyme.

Another embodiment of the invention is a method of screening for agents which decrease extracellular matrix degradation. A test compound is contacted with a polynucleotide encoding a transketolase-like enzyme polypeptide, wherein the polynucleotide comprises a nucleotide sequence selected from the group consisting of:

nucleotide sequences which are at least about 50% identical to the nucleotide sequence shown in SEQ ID NO: 1;

the nucleotide sequence shown in SEQ ID NO: 1;

nucleotide sequences which are at least about 50% identical to the nucleotide sequence shown in SEQ ID NO: 6; and the nucleotide sequence shown in SEQ ID NO: 6.

Binding of the test compound to the polynucleotide is detected. A test compound which binds to the polynucleotide is identified as a potential agent for decreasing extracellular matrix degradation. The agent can work by decreasing the amount of the transketolase-like enzyme through interacting with the transketolase-like enzyme mRNA.

Another embodiment of the invention is a method of screening for agents which regulate extracellular matrix degradation. A test compound is contacted with a transketolase-like enzyme polypeptide comprising an amino acid sequence selected from the group consisting of:

amino acid sequences which are at least about 70% identical to the amino acid sequence shown in SEQ ID NO: 2; and the amino acid sequence shown in SEQ ID NO: 2.

A transketolase-like enzyme activity of the polypeptide is detected. A test compound which increases transketolase-like enzyme activity of the polypeptide relative to transketolase-like enzyme activity in the absence of the test compound is thereby identified as a potential agent for increasing extracellular matrix degradation. A test compound which decreases transketolase-like enzyme activity of the polypeptide relative to transketolase-like enzyme activity in the absence of the test compound is thereby identified as a potential agent for decreasing extracellular matrix degradation.

Even another embodiment of the invention is a method of screening for agents which decrease extracellular matrix degradation. A test compound is contacted with a transketolase-like enzyme product of a polynucleotide which comprises a nucleotide sequence selected from the group consisting of:

nucleotide sequences which are at least about 50% identical to the nucleotide sequence shown in SEQ ID NO: 1;

the nucleotide sequence shown in SEQ ID NO: 1;

nucleotide sequences which are at least about 50% identical to the nucleotide sequence shown in SEQ ID NO: 6; and the nucleotide sequence shown in SEQ ID NO: 6.

Binding of the test compound to the transketolase-like enzyme product is detected. A test compound which binds to the transketolase-like enzyme product is thereby identified as a potential agent for decreasing extracellular matrix degradation.

Still another embodiment of the invention is a method of reducing extracellular matrix degradation. A cell is contacted with a reagent which specifically binds to a polynucleotide encoding a transketolase-like enzyme polypeptide or the product encoded by the polynucleotide, wherein the polynucleotide comprises a nucleotide sequence selected from the group consisting of:

nucleotide sequences which are at least about 50% identical to the nucleotide sequence shown in SEQ ID NO: 1;

the nucleotide sequence shown in SEQ ID NO: 1;

nucleotide sequences which are at least about 50% identical to the nucleotide sequence shown in SEQ ID NO: 6;

the nucleotide sequence shown in SEQ ID NO: 6.

Transketolase-like enzyme activity in the cell is thereby decreased.

The invention thus provides a human transketolase-like enzyme which can be used to identify test compounds which may act, for example, as agonists or antagonists at the enzyme's active site. Human transketolase-like enzyme and fragments thereof also are useful in raising specific antibodies which can block the enzyme and effectively reduce its activity.

BRIEF DESCRIPTION OF THE DRAWINGS

FIG. 1 shows the DNA-sequence encoding a transketolase-like enzyme polypeptide.

FIG. 2 shows the amino acid sequence deduced from the DNA-sequence of FIG. 1.

FIG. 3 shows the amino acid sequence of a mouse protein identified with SwissProt Accession No. P40142.

FIG. 4 shows the amino acid sequence of yeast transketolase.

FIG. 5 shows the amino acid sequence of the CG10231 gene product of D. melanogaster.

FIG. 6 shows the DNA-sequence encoding a transketolase-like enzyme polypeptide.

FIG. 7 shows the BLASTP alignment of transketolase-like enzyme polypeptide of FIG. 2 with the mouse protein identified with SwissProt Accession No. P40142 of FIG. 3.

FIG. 8 shows the alignment pattern for transketolase-like enzyme polypeptide of FIG. 2. The histidine in this sequence is missing, and this histidine residue (italics) appears to function in proton transfer during catalysis.

FIG. 9 shows the alignment of transketolase-like enzyme polypeptide of FIG. 2 with yeast transketolase of FIG. 4.

DETAILED DESCRIPTION OF THE INVENTION

The invention relates to an isolated polynucleotide encoding a transketolase-like enzyme polypeptide and being selected from the group consisting of:

a) a polynucleotide encoding a transketolase-like enzyme polypeptide comprising an amino acid sequence selected from the group consisting of:
amino acid sequences which are at least about 70% identical to the amino acid sequence shown in SEQ ID NO: 2; and
the amino acid sequence shown in SEQ ID NO: 2.

b) a polynucleotide comprising the sequence of SEQ ID NOS: 1 or 6;

c) a polynucleotide which hybridizes under stringent conditions to a polynucleotide specified in (a) and (b);

d) a polynucleotide the sequence of which deviates from the polynucleotide sequences specified in (a) to (c) due to the degeneration of the genetic code; and e) a polynucleotide which represents a fragment, derivative or allelic variation of a polynucleotide sequence specified in (a) to (d).

Furthermore, it has been discovered by the present applicant that a novel transketolase-like enzyme, particularly a human transketolase-like enzyme, is a discovery of the present invention. Human transketolase-like enzyme comprises the amino acid sequence shown in SEQ ID NO:2. Human transketolase-like enzyme was identified by searching human sequences with the CG10231 gene product of D. melanogaster (SEQ ID NO:5). A coding sequence for human transketolase-like enzyme (SEQ ID NO:6) is found in the human clone identified with GenBank Accession No. gb|AC011998.3|AC011998 Homo sapiens clone RP11-318F5 (working draft sequence, 9 unordered pieces; version AC011998.3; SEQ ID NO:1). Human transketolase-like enzyme is 67% identical over 614 amino acids to the mouse protein identified with SwissProt Accession No. P40142 and annotated as a transketolase (FIG. 1). Human transketolase-like enzyme as shown in SEQ ID NO:2 contains a transketolase region from residue 19 to 268 (bold and underlined in FIG. 3), a transketolase region from residue 310 to 615 (bold in FIG. 3), and an ATP/GTP binding region from residue 594 to 602 (italics in FIG. 3).

The human transketolase-like enzyme of the invention is expected to be useful for the same purposes as previously identified transketolases. Thus, human transketolase-like enzyme can be used in therapeutic methods to treat disorders such as cancer, anemia, and end-stage renal disease, including sensory periphery neuropathy associated with uremia. Human transketolase-like enzyme also can be used to screen for human transketolase-like enzyme agonists and antagonists.

Polypeptides

Transketolase-like enzyme polypeptides according to the invention comprise at least 14, 15, 20, 25, 30, 35, 40, 45, 50, 75, 100, 125, 150, 175, 200, 250, 300, 350, 400, 450, 500, 550, or 600 contiguous amino acids selected from the amino acid sequence shown in SEQ ID NO:2 or a biologically active variant thereof, as defined below. A transketolase-like enzyme polypeptide of the invention therefore can be a portion of a transketolase-like enzyme protein, a full-length transketolase-like enzyme protein, or a fusion protein comprising all or a portion of a transketolase-like enzyme protein.

Biologically Active Variants

Transketolase-like enzyme polypeptide variants which are biologically active, i.e., retain the ability to bind thiamin pyrophosphate, to transfer a glycoaldehyde group from D-xylulose 5-phosphate to D-ribose 5-phosphate, or to carry out other transketolase-like activities, also are transketolase-like enzyme polypeptides. Preferably, naturally or non-naturally occurring transketolase-like enzyme polypeptide variants have amino acid sequences which are at least about 70, preferably about 75, 90, 96, or 98% identical to the amino acid sequence shown in SEQ ID NO:2 or a fragment thereof. Percent identity between a putative transketolase-like enzyme polypeptide variant and an amino acid sequence of SEQ ID NO:2 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a transketolase-like enzyme polypeptide can be found using computer programs well known in the art, such as DNASTAR software. Whether an amino acid change results in a biologically active transketolase-like enzyme polypeptide can readily be determined by assaying for transketolase activity or for ATP or GTP binding, as described for example, in the specific Examples, below.

Fusion Proteins

Fusion proteins are useful for generating antibodies against transketolase-like enzyme polypeptide amino acid sequences and for use in various assay systems. For example, fusion proteins can be used to identify proteins which interact with portions of a transketolase-like enzyme polypeptide. Protein affinity chromatography or library-based assays for protein-protein interactions, such as the yeast two-hybrid or phage display systems, can be used for this purpose. Such methods are well known in the art and also can be used as drug screens.

A transketolase-like enzyme polypeptide fusion protein comprises two polypeptide segments fused together by means of a peptide bond. The first polypeptide segment comprises at least 14, 15, 20, 25, 30, 35, 40, 45, 50, 75, 100, 125, 150, 175, 200, 250, 300, 350, 400, 450, 500, 550, or 600 contiguous amino acids of SEQ ID NO:2 or of a biologically active variant, such as those described above. The first polypeptide segment also can comprise full-length transketolase-like enzyme protein.

The second polypeptide segment can be a full-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BPI6 protein fusions. A fusion protein also can be engineered to contain a cleavage site located between the transketolase-like enzyme polypeptide-encoding sequence and the heterologous protein sequence, so that the transketolase-like enzyme polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO:6 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human transketolase-like enzyme polypeptide can be obtained using transketolase-like enzyme polypeptide polynucleotides (described below) to make suitable probes or primers for screening cDNA expression libraries from other species, such as mice, monkeys, or yeast, identifying cDNAs which encode homologs of transketolase-like enzyme polypeptide, and expressing the cDNAs as is known in the art.

Polynucleotides

A transketolase-like enzyme polynucleotide can be single- or double-stranded and comprises a coding sequence or the complement of a coding sequence for a transketolase-like enzyme polypeptide. A coding sequence for human transketolase-like enzyme is shown in SEQ ID NO:6; this coding sequence is contained within SEQ ID NO:1.

Degenerate nucleotide sequences encoding human transketolase-like enzyme polypeptides, as well as homologous nucleotide sequences which are at least about 50, preferably about 75, 90, 96, or 98% identical to the nucleotide sequence shown in SEQ ID NOS:1 and 6 also are transketolase-like enzyme polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of transketolase-like enzyme polynucleotides which encode biologically active transketolase-like enzyme polypeptides also are Transketolase-like enzyme polynucleotides.

Identification of Polynucleotide Variants and Homologs

Variants and homologs of the transketolase-like enzyme polynucleotides described above also are transketolase-like enzyme polynucleotides. Typically, homologous Transketolase-like enzyme polynucleotide sequences can be identified by hybridization of candidate polynucleotides to known transketolase-like enzyme polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the transketolase-like enzyme polynucleotides disclosed herein also can be identified by making suitable probes or primers and screening cDNA expression libraries from other species, such as mice, monkeys, or yeast. Human variants of transketolase-like enzyme polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human transketolase-like enzyme polynucleotides or transketolase-like enzyme polynucleotides of other species can therefore be identified by hybridizing a putative homologous transketolase-like enzyme polynucleotide with a polynucleotide having a nucleotide sequence of SEQ ID NO:1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to transketolase-like enzyme polynucleotides or their complements following stringent hybridization and/or wash conditions also are transketolase-like enzyme polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a transketolase-like enzyme polynucleotide having a nucleotide sequence shown in SEQ ID NO:1 or 6 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m=81.5° C.-16.6(\log_{10}[Na^+])+0.41(\% G+C)-0.63(\% \text{formamide})-600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A naturally occurring transketolase-like enzyme polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated transketolase-like enzyme polynucleotides. For example, restriction enzymes and probes can be used to isolate polynucleotide fragments which comprises transketolase-like enzyme nucleotide sequences. Isolated polynucleotides are in preparations which are free or at least 70, 80, or 90% free of other molecules.

Transketolase-like enzyme cDNA molecules can be made with standard molecular biology techniques, using transketolase-like enzyme mRNA as a template. Transketolase-like enzyme cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesizes transketolase-like enzyme polynucleotides. The degeneracy of the genetic code allows alternate nucleotide sequences to be synthesized which will encode a transketolase-like enzyme polypeptide having, for example, an amino acid sequence shown in SEQ ID NO:2 or a biologically active variant thereof.

Extending Polynucleotides

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

Transketolase-like enzyme polypeptides can be obtained, for example, by purification from human cells, by expression of transketolase-like enzyme polynucleotides, or by direct chemical synthesis.

Protein Purification

Transketolase-like enzyme polypeptides can be purified from any human cell which expresses the enzyme, including host cells which have been transfected with transketolase-like enzyme expression constructs. A purified transketolase-like enzyme polypeptide is separated from other compounds which normally associate with the transketolase-like enzyme polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified transketolase-like enzyme polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express a transketolase-like enzyme polynucleotide, the polynucleotide can be inserted into an expression vector which contains the necessary elements for the transcription and translation of the inserted coding sequence. Methods which are well known to those skilled in the art can be used to construct expression vectors containing sequences encoding transketolase-like enzyme polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a transketolase-like enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a transketolase-like enzyme polypeptide, vectors based on SV40 or EBV can be used with an appropriate selectable marker.

Bacterial and Yeast Expression Systems

In bacterial systems, a number of expression vectors can be selected depending upon the use intended for the transketolase-like enzyme polypeptide. For example, when a large quantity of a transketolase-like enzyme polypeptide is needed for the induction of antibodies, vectors which direct high level expression of fusion proteins that are readily purified can be used. Such vectors include, but are not limited to, multifunctional E. coli cloning and expression vectors such as BLUESCRIPT (Stratagene). In a BLUESCRIPT vector, a sequence encoding the transketolase-like enzyme polypeptide can be ligated into the vector in frame with sequences for the amino-terminal Met and the subsequent 7 residues of β-galactosidase so that a hybrid protein is produced. pIN vectors (Van Heeke & Schuster, J. Biol. Chem. 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast Saccharomyces cerevisiae, a number of vectors containing constitutive or inducible promoters such as alpha factor, alcohol oxidase, and PGH can be used. For reviews, see Ausubel et al. (1989) and Grant et al., Methods Enzymol. 153, 516–544, 1987.

Plant and Insect Expression Systems

If plant expression vectors are used, the expression of sequences encoding transketolase-like enzyme polypeptides can be driven by any of a number of promoters. For example, viral promoters such as the 35S and 19S promoters of CaMV can be used alone or in combination with the omega leader sequence from TMV (Takamatsu, EMBO J. 6, 307–311, 1987). Alternatively, plant promoters such as the small subunit of RUBISCO or heat shock promoters can be used (Coruzzi et al., EMBO J. 3, 1671–1680, 1984; Broglie et al., Science 224, 838–843, 1984; Winter et al., Results Probl. Cell Differ. 17, 85–105, 1991). These constructs can be introduced into plant cells by direct DNA transformation or by pathogen-mediated transfection. Such techniques are described in a number of generally available reviews (e.g., Hobbs or Murray, in McGRAW HILL YEARBOOK OF SCIENCE AND TECHNOLOGY, McGraw Hill, New York, N.Y., pp. 191–196, 1992).

An insect system also can be used to express a transketolase-like enzyme polypeptide. For example, in one such system Autographa californica nuclear polyhedrosis virus (AcNPV) is used as a vector to express foreign genes in Spodoptera frugiperda cells or in Trichoplusia larvae. Sequences encoding transketolase-like enzyme polypeptides can be cloned into a non-essential region of the virus, such as the polyhedrin gene, and placed under control of the polyhedrin promoter. Successful insertion of transketolase-like enzyme polypeptides will render the polyhedrin gene inactive and produce recombinant virus lacking coat protein. The recombinant viruses can then be used to infect S. frugiperda cells or Trichoplusia larvae in which transketolase-like enzyme polypeptides can be expressed (Engelhard et al., Proc. Nat. Acad. Sci. 91, 3224–3227, 1994).

Mammalian Expression Systems

A number of viral-based expression systems can be used to express transketolase-like enzyme polypeptides in mammalian host cells. For example, if an adenovirus is used as an expression vector, sequences encoding transketolase-like enzyme polypeptides can be ligated into an adenovirus transcription/translation complex comprising the late promoter and tripartite leader sequence. Insertion in a non-essential E1 or E3 region of the viral genome can be used to obtain a viable virus which is capable of expressing a transketolase-like enzyme polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding transketolase-like enzyme polypeptides. Such signals include the ATG initiation codon and adjacent sequences. In cases where sequences encoding a transketolase-like enzyme polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process the expressed transketolase-like enzyme polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express transketolase-like enzyme polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced transketolase-like enzyme sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines. These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980) genes which can be employed in tk$^-$ or aprt$^-$ cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567–70, 1980), npt confers resistance to the aminoglycosides, neomycin and G-418 (Colbere-Garapin et al., *J. Mol. Biol.* 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, *Proc. Natl. Acad. Sci.* 85, 8047–51, 1988). Visible markers such as anthocyanins, _-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression

Although the presence of marker gene expression suggests that the transketolase-like enzyme polynucleotide is also present, its presence and expression may need to be confirmed. For example, if a sequence encoding a transketolase-like enzyme polypeptide is inserted within a marker gene sequence, transformed cells containing sequences which encode a transketolase-like enzyme polypeptide can be identified by the absence of marker gene function. Alternatively, a marker gene can be placed in tandem with a sequence encoding a transketolase-like enzyme polypeptide under the control of a single promoter. Expression of the marker gene in response to induction or selection usually indicates expression of the transketolase-like enzyme polynucleotide.

Alternatively, host cells which contain a transketolase-like enzyme polynucleotide and which express a transketolase-like enzyme polypeptide can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding a transketolase-like enzyme polypeptide can be detected by DNA-DNA or DNA-RNA hybridization or amplification using probes or fragments or fragments of polynucleotides encoding a transketolase-like enzyme polypeptide. Nucleic acid amplification-based assays involve the use of oligonucleotides selected from sequences encoding a transketolase-like enzyme polypeptide to detect transformants which contain a transketolase-like enzyme polynucleotide.

A variety of protocols for detecting and measuring the expression of a transketolase-like enzyme polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a transketolase-like enzyme polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding transketolase-like enzyme polypeptides include oligo-labeling, nick translation, end-labeling, or PCR amplification using a labeled nucleotide. Alternatively, sequences encoding a transketolase-like enzyme polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding a transketolase-like enzyme polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode transketolase-like enzyme polypeptides can be designed to contain signal sequences which direct secretion of soluble transketolase-like enzyme polypeptides through a prokaryotic or eukaryotic cell membrane or which direct the membrane insertion of membrane-bound transketolase-like enzyme polypeptide.

As discussed above, other constructions can be used to join a sequence encoding a transketolase-like enzyme polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the transketolase-like enzyme polypeptide also can be used to facilitate purification. One such expression vector provides for expression of a fusion protein containing a transketolase-like enzyme polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif.* 3, 263–281, 1992), while the enterokinase cleavage site provides a means for purifying the transketolase-like enzyme polypeptide from the fusion protein. Vectors which contain fusion proteins are disclosed in Kroll et al., *DNA Cell Biol.* 12, 441–453, 1993.

Chemical Synthesis

Sequences encoding a transketolase-like enzyme polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, a transketolase-like enzyme polypeptide itself can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of transketolase-like enzyme polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic transketolase-like enzyme polypeptide can be confirmed by amino acid analysis or sequencing (e.g., the Edman degradation procedure; see Creighton, supra). Additionally, any portion of the amino acid sequence of the transketolase-like enzyme polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce transketolase-like enzyme polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter transketolase-like enzyme polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a transketolase-like enzyme polypeptide. "Antibody" as used herein includes intact immunoglobulin molecules, as well as fragments thereof, such as Fab, F(ab')$_2$, and Fv, which are capable of binding an epitope of a transketolase-like enzyme polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a transketolase-like enzyme polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to a transketolase-like enzyme polypeptide provides a detection signal at least 5-, 10-, or 20-fold higher than a detection signal provided with other proteins when used in an immunochemical assay. Preferably, antibodies which specifically bind to transketolase-like enzyme polypeptides do not detect other proteins in immunochemical assays and can immunoprecipitate a transketolase-like enzyme polypeptide from solution.

Transketolase-like enzyme polypeptides can be used to immunize a mammal, such as a mouse, rat, rabbit, guinea pig, monkey, or human, to produce polyclonal antibodies. If desired, a transketolase-like enzyme polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies which specifically bind to a transketolase-like enzyme polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies which specifically bind to a transketolase-like enzyme polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to transketolase-like enzyme polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to transketolase-like enzyme polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which a transketolase-like enzyme polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of transketolase-like enzyme gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of transketolase-like enzyme gene expression can be obtained by designing antisense oligonucleotides which will form duplexes to the control, 5', or regulatory regions of the transketolase-like enzyme gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of a transketolase-like enzyme polynucleotide. Antisense oligonucleotides which comprise, for example, 2, 3, 4, or 5 or more stretches of contiguous nucleotides which are precisely complementary to a transketolase-like enzyme polynucleotide, each separated by a stretch of contiguous nucleotides which are not complementary to adjacent transketolase-like enzyme nucleotides, can provide sufficient targeting specificity for transketolase-like enzyme mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular transketolase-like enzyme polynucleotide sequence.

Antisense oligonucleotides can be modified without affecting their ability to hybridize to a transketolase-like enzyme polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a transketolase-like enzyme polynucleotide can be used to generate ribozymes which will specifically bind to mRNA transcribed from the transketolase-like enzyme polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a transketolase-like enzyme RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate transketolase-like enzyme RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease transketolase-like enzyme expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Screening Methods

The invention provides assays for screening test compounds which bind to or modulate the activity of a transketolase-like enzyme polypeptide or a transketolase-like enzyme polynucleotide. A test compound preferably binds to a transketolase-like enzyme polypeptide or polynucleotide. More preferably, a test compound decreases or increases the ability of human transketolase-like enzyme to bind a thiamin pyrophosphate or decreases or increases transketolase or transketolase-like activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990; Felici, *J. Mol. Biol.* 222, 301–310, 1991; and Ladner, U.S. Pat. No. 5,223,409).

High Throughput Screening

Test compounds can be screened for the ability to bind to transketolase-like enzyme polypeptides or polynucleotides or to affect transketolase-like enzyme activity or transketolase-like enzyme gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies, for example, the ATP/GTP binding site of the enzyme or the active site of the transketolase-like enzyme polypeptide, such that normal biological activity is prevented. Examples of such small molecules include, but are not limited to, small peptides or peptide-like molecules.

In binding assays, either the test compound or the transketolase-like enzyme polypeptide can comprise a detectable label, such as a fluorescent, radioisotopic, chemiluminescent, or enzymatic label, such as horseradish peroxidase, alkaline phosphatase, or luciferase. Detection of a test compound which is bound to the transketolase-like enzyme polypeptide can then be accomplished, for example, by direct counting of radioemmission, by scintillation counting, or by determining conversion of an appropriate substrate to a detectable product.

Alternatively, binding of a test compound to a transketolase-like enzyme polypeptide can be determined without labeling either of the interactants. For example, a microphysiometer can be used to detect binding of a test compound with a transketolase-like enzyme polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a transketolase-like enzyme polypeptide (McConnell et al., *Science* 257, 1906–1912, 1992).

Determining the ability of a test compound to bind to a transketolase-like enzyme polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a transketolase-like enzyme polypeptide can be used as a "bait protein" in a two-hybrid assay or three-hybrid assay (see, e.g., U.S. Pat. No. 5,283,317; Zervos et al., Cell 72, 223–232, 1993; Madura et al., J. Biol. Chem. 268, 12046–12054, 1993; Bartel et al., BioTechniques 14, 920–924, 1993; Iwabuchi et al., Oncogene 8, 1693–1696, 1993; and Brent WO94/10300), to identify other proteins which bind to or interact with the transketolase-like enzyme polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a transketolase-like enzyme polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the transketolase-like enzyme polypeptide.

It may be desirable to immobilize either the transketolase-like enzyme polypeptide (or polynucleotide) or the test compound to facilitate separation of bound from unbound forms of one or both of the interactants, as well as to accommodate automation of the assay. Thus, either the transketolase-like enzyme polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the transketolase-like enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a transketolase-like enzyme polypeptide (or polynucleotide) can be accomplished in any vessel suitable for containing the reactants. Examples of such vessels include microtiter plates, test tubes, and microcentrifuge tubes.

In one embodiment, the transketolase-like enzyme polypeptide is a fusion protein comprising a domain that allows the transketolase-like enzyme polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed transketolase-like enzyme polypeptide; the mixture is then incubated under conditions conducive to complex formation (e.g., at physiological conditions for salt and pH). Following incubation, the beads or microtiter plate wells are washed to remove any unbound components.

Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a transketolase-like enzyme polypeptide (or polynucleotide) or a test compound can be immobilized utilizing conjugation of biotin and streptavidin. Biotinylated transketolase-like enzyme polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a transketolase-like enzyme polypeptide, polynucleotide, or a test compound, but which do not interfere with a desired binding site, such as the ATP/GTP binding site or the active site of the transketolase-like enzyme polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the transketolase-like enzyme polypeptide or test compound, enzyme-linked assays which rely on detecting an activity of the transketolase-like enzyme polypeptide, and SDS gel electrophoresis under non-reducing conditions.

Screening for test compounds which bind to a transketolase-like enzyme polypeptide or polynucleotide also can be carried out in an intact cell. Any cell which comprises a transketolase-like enzyme polypeptide or polynucleotide can be used in a cell-based assay system. A transketolase-like enzyme polynucleotide can be naturally occurring in the cell or can be introduced using techniques such as those described above. Binding of the test compound to a transketolase-like enzyme polypeptide or polynucleotide is determined as described above.

Enzyme Assays

Test compounds can be tested for the ability to increase or decrease the transketolase or transketolase-like activity of a human transketolase-like enzyme polypeptide. Transketolase activity can be measured, for example, as described in Pietrzak & Baczyk, Miner. Electrolyte Metab. 23, 277–82 (1997) or Jamieson et al., Clin. Nutr. 18, 87–91 (1999).

Enzyme assays can be carried out after contacting either a purified transketolase-like enzyme polypeptide, a cell membrane preparation, or an intact cell with a test compound. A test compound which decreases a transketolase activity of a transketolase-like enzyme polypeptide by at least about 10, preferably about 50, more preferably about 75, 90, or 100% is identified as a potential therapeutic agent for decreasing transketolase-like enzyme activity. A test compound which increases a transketolase activity of a human transketolase-like enzyme polypeptide by at least about 10, preferably about 50, more preferably about 75, 90, or 100% is identified as a potential therapeutic agent for increasing human transketolase-like enzyme activity.

Gene Expression

In another embodiment, test compounds which increase or decrease transketolase-like enzyme gene expression are identified. A transketolase-like enzyme polynucleotide is contacted with a test compound, and the expression of an RNA or polypeptide product of the transketolase-like enzyme polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of transketolase-like enzyme mRNA or polypeptide expression in the cells can be determined by methods well known in the art for detecting mRNA or polypeptide. Either qualitative or quantitative methods can be used. The presence of polypeptide products of a transketolase-like enzyme polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a transketolase-like enzyme polypeptide.

Such screening can be carried out either in a cell-free assay system or in an intact cell. Any cell which expresses a transketolase-like enzyme polynucleotide can be used in a cell-based assay system. The transketolase-like enzyme polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions which can be administered to a patient to achieve a therapeutic effect. Pharmaceutical compositions of the invention can comprise, for example, a transketolase-like enzyme polypeptide, transketolase-like enzyme polynucleotide, ribozymes or antisense oligonucleotides, antibodies which specifically bind to a transketolase-like enzyme polypeptide, or mimetics, agonists, antagonists, or inhibitors of a transketolase-like enzyme polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

Transketolase activity is increased in tumors (Boros et al., *Anticancer Res.* 18, 595–602, 1998). Thus, inhibition of human transketolase-like enzyme is expected to be useful for treating cancer. Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Transketolase activity is decreased, for example, in dialysis patients with end-stage renal disease and in anemic patients (Pietrzak & Baczyk, *Miner. Electrolyte Metab.* 23, 277–82, 1997; Descombes et al., *Clin. Nephrol.* 35, 171–75, 1991). Transketolase activity also is decreased in uremic patients with sensory peripheral neuropathies. Thus, increased activity or increased levels of human transketolase-like enzyme is expected to be useful for treating such disorders.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a transketolase-like enzyme polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects transketolase-like enzyme activity can be administered to a human cell, either in vitro or in vivo, to reduce transketolase-like enzyme activity. The reagent preferably binds to an expression product of a human transketolase-like enzyme gene. If the expression product is a protein, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 $\mu$g of DNA per 16 nmole of liposome delivered to about $10^6$ cells, more preferably about 1.0 $\mu$g of DNA per 16 nmole of liposome delivered to about $10^6$ cells, and even more preferably about 2.0 $\mu$g of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 $\mu$g to about 10 $\mu$g of polynucleotide is combined with about 8 nmol of liposomes, more preferably from about 0.5 $\mu$g to about 5 $\mu$g of polynucleotides are combined with about 8 nmol liposomes, and even more preferably about 1.0 $\mu$g of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient which increases or decreases transketolase-like enzyme activity relative to the transketolase-like enzyme activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides which express antisense oligonucleotides or ribozymes can be introduced into cells by a variety of methods, as described above.

Preferably, a reagent reduces expression of a transketolase-like enzyme gene or the activity of a transketolase-like enzyme polypeptide by at least about 10, preferably about 50, more preferably about 75, 90, or 100% relative to the absence of the reagent. The effectiveness of the mechanism chosen to decrease the level of expression of a transketolase-like enzyme gene or the activity of a transketolase-like enzyme polypeptide can be assessed using methods well known in the art, such as hybridization of nucleotide probes to transketolase-like enzyme-specific mRNA, quantitative RT-PCR, immunologic detection of a transketolase-like enzyme polypeptide, or measurement of transketolase-like enzyme activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human transketolase-like enzyme also can be used in diagnostic assays for detecting diseases and abnormalities or susceptibility to diseases and abnormalities related to the presence of mutations in the nucleic acid sequences which encode the enzyme. For example, differences can be determined between the cDNA or genomic sequence encoding transketolase-like enzyme in individuals afflicted with a disease and in normal individuals, If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR.

The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S 1 protection or the chemical cleavage method (e.g., Cotton et al., *Proc. Natl. Acad. Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of a transketolase-like enzyme also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Detection of Transketolase-like Enzyme Activity

The polynucleotide of SEQ ID NO: 1 is inserted into the expression vector pCEV4 and the expression vector pCEV4-transketolase-like enzyme polypeptide obtained is transfected into human embryonic kidney 293 cells. The cells are cultivated under conventional conditions. The cells are washed three times with a cold isotonic buffer and lysed by resuspending and vortexing in a lysis buffer containing 20 mmol/L Tris-Cl (pH 7,5), 1 mmol/L dithiothreitol, 1 mmol/L potassium EDTA, 0,2 g/L Triton X-100, 0,2 g/L sodium deoxycholate and 0,2 mmol/L phenylmethylsulfonyl fluoride. The protein concentration of the clarified supernatant is determined using the Bio-Rad Protein Assay (Bio-Rad, Hercules Calif.).

Transketolase activity is measured by using a conventional enzyme-linked method under conditions in which coupling enzymes are not limiting. Reactions are initiated by the addition of 0,36 mg total protein/mL of reaction mix to an otherwise complete reaction mix of 100 mmol/L Tris-Cl (pH 7,5), 10 mmol/L ribose 5-phosphate, 2 mmol/L xylulose 5 phosphate, 1,2 mmol/L MgCl2, 0,1 mmol/L NADH, 2000 U/L glycerol-3-phosphate dehydrogenase and triose phosphate isomerase. Reactions were conducted at 37° C. The oxidation of NADH, which is directly proportional to transketolase activity, was followed by monitoring the decrease in absorbance at 340 nm using a Beckman DC-70 sspectrophotometer (Beckman, Palo Alto, Calif.). Activity is expressed as nmol/(min mg protein). It is shown that the polypeptide of SEQ ID NO: 2 has transketolase-like enzyme activity.

EXAMPLE 2

Expression of Recombinant Human Transketolase-like Enzyme

To produce large quantities of human transketolase-like enzyme polypeptides in yeast, the *Pichia pastoris* expression vector pPICZB (Invitrogen, San Diego, Calif.) is used. The human transketolase-like enzyme encoding DNA sequence is the nucleotide sequence shown in SEQ ID NO:6. Before insertion into vector pPICZB, the DNA sequence is modified by well known methods in such a way that it contains at its 5'-end an initiation codon and at its 3'-end an enterokinase cleavage site, a His6 reporter tag, and a termination codon. Recognition sequences for restriction endonucleases are added at both termini. After digestion of the multiple cloning site of pPICZ B with the corresponding restriction enzymes, the modified human transketolase-like enzyme polypeptide-encoding DNA sequence is ligated into pPICZB. This expression vector is designed for inducible expression in *Pichia pastoris*, and expression is driven by a yeast promoter. The resulting pPICZ/md-His6 vector is used to transform the yeast. The yeast is cultivated under usual conditions in shake flasks, and the recombinantly produced protein is isolated from the culture by affinity chromatography (Ni-NTA-Resin) in the presence of 8 M urea. The bound polypeptide is eluted with buffer, pH 3.5, and neutralized. Separation of the human transketolase-like enzyme polypeptide from the His6 reporter tag is accomplished by site-specific proteolysis using enterokinase (Invitrogen, San Diego, Calif.) according to manufacturer s instructions. Purified human transketolase-like enzyme polypeptide is obtained.

EXAMPLE 3

Identification of Test Compounds That Bind to Transketolase-like Enzyme Polypeptides Purified transketolase-like enzyme polypeptides comprising a glutathione-S-transferase protein and absorbed onto glutathione-derivatized wells of 96-well microtiter plates are contacted with test compounds from a small molecule library at pH 7.0 in a physiological buffer solution. Transketolase-like enzyme polypeptides comprise the amino acid sequence shown in SEQ ID NO:2. The test compounds comprise a fluorescent tag. The samples are incubated for 5 minutes to one hour. Control samples are incubated in the absence of a test compound.

The buffer solution containing the test compounds is washed from the wells. Binding of a test compound to a transketolase-like enzyme polypeptide is detected by fluorescence measurements of the contents of the wells. A test compound which increases the fluorescence in a well by at least 15% relative to fluorescence of a well in which a test compound is not incubated is identified as a compound which binds to a transketolase-like enzyme polypeptide.

EXAMPLE 4

Identification of a Test Compound which Decreases Transketolase-like Enzyme Gene Expression A test compound is administered to a culture of human cells transfected with a transketolase-like enzyme expression construct and incubated at 37° C. for 10 to 45 minutes. A culture of the same type of cells which have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled transketolase-like enzyme-specific probe at 65° C. in Express-hyb (CLONTECH). The probe comprises at least 11 contiguous nucleotides selected from the complement of SEQ ID NO:6. A test compound which decreases the transketolase-like enzyme-specific signal relative to the signal obtained in the absence of the test compound is identified as an inhibitor of transketolase-like enzyme gene expression.

EXAMPLE 5

Treatment of Breast Cancer with a Reagent which Specifically Binds to a Transketolase-like Enzyme Gene Product Synthesis of antisense transketolase-like enzyme oligonucleotides comprising at least 11 contiguous nucleotides selected from the complement of SEQ ID NO:6 is performed on a Pharmacia Gene Assembler series synthesizer using the phosphoramidite procedure (Uhlmann et al., *Chem. Rev.* 90, 534–83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the *Limulus* Amebocyte Assay (Bang, *Biol. Bull.* (Woods Hole, Mass.) 105, 361–362, 1953).

The antisense oligonucleotides in an aqueous solution are administered to a patient with breast cancer by direct injection into the breast tumor. The size of the patient's breast tumor is decreased.

What is claimed is:

1. A method of screening for candidate modulators of transketolase activity comprising the steps of:

contacting a protein comprising the amino acid sequence shown in SEQ ID NO:2 with a test compound;

assaying for binding between the protein and the test compound; and identifying a test compound that binds to the protein as a candidate modulator of transketolase activity that may be useful for regulating activity of the protein.

2. The method of claim 1 wherein either the test compound or the protein comprises a detectable label.

3. The method of claim 1 wherein either the test compound or the protein is bound to a solid support.

* * * * *

SEQUENCE LISTING

<160> NUMBER OF SEQ ID NOS: 6

<210> SEQ ID NO 1
<211> LENGTH: 3540
<212> TYPE: DNA
<213> ORGANISM: Human

<400> SEQUENCE: 1

```
tttaacgtga agttaaggta agaattattg ctcaagaaac caagaggttt aacatcgcaa      60
tatgggaagg tatgatatat tatcattgtg tttttttaa ttgttgtttt attgatgaca     120
aaccataacc ttggcctgct agaagagttc aatggcacaa atttagtttt ttttgtttta     180
gacggagtct cgctctgtct cccaggctgg agtgcagtgg cacaatctgg gctcactgca     240
agctccacct cccaggttca cgccattctc ctgcctcagc ctcccgagta gctgggacta     300
caggtgccca tcaccacgcc cagctaattt tttgtattt ttagtagaca cggggtttca     360
ccgtgttagc caggatggtc tcgaactcct gaccttgtga tccgcctgcc tcggcctccc     420
aaagtgctgg gattacaggt gtgagccaca gcacccggcc cacaaattta gttttttaaa     480
gtaagtaact ttgtcttaaa aatgatttgt agtaatagtc attaaaagat aaactgaggc     540
acattaaaat attaaagcat ttatttgacc attcagtgat tcatgaatct ggtagctcct     600
gataaaggag ccaaggagaa ggcttttata gggtgaattt ggaagcaaag gaaagatatt     660
tgattggtta aagtggagta ctagacttat ttgggtcatc ccagtggaaa gtccccagtt     720
agaagttagc tggcagtttc tgattgatta agcttaaatt tccttttat catttacact     780 gatttgggtt tcctttcctt aggtaggaac tcatggagct gaagctacct cagcctactg     840
gccttctaat tatttcaaca cagaaatagt actttacggc acactggagt tgcaattcta     900
ttctgcaatt gggtggtttc agatttgttc ttcctataaa ttttggtcaa attagtcatt     960
gcatttcttt ctataagtct gagattcaga tatttggttg ctctgagaaa gtctctgttg    1020
agatagcatt gccatactgg tcagattgaa agtgactttg tatcctttct attaatgttc    1080
tgatatgaaa gagtgatgac tcggatatag tgttaatgca ttaaaaaagc acagcctgac    1140
aaatcgcttc ctataataca cagaaaatg tctagtcttg aatttataac acagggaaag    1200
```

-continued

```
gtaaaaaatt taattatgct tcctaatgtt gaacatgcac gtgacaaagt aaatactaaa   1260
aatccattca gctgggcgtg gacagggaga gggaacggtg cacatcagag ggtgcaggct   1320
actccaacgt ttccgtttcc tcagtctcgc gggaagctcc gttgtgggcg ccccggctgg   1380
tggctgagct caggccttca ggcagagggg aggcgagggc ggggcggtca cgtgagagca   1440
ctgccgcggt gggttgtggg ggtgctgcgg cgccgtttgc tttgccaaac cgacaaaaga   1500
gagatgatgg ccaacgacgc caagcccgac gtgaagaccg tgcaggtgct gcgggacaca   1560
gccaaccgcc tgcggatcca ttccatcagg gccacgtgtg cctctggttc tggccagctc   1620
acgtcgtgct gcagtgcagc ggaggtcgtg tctgtcctct tcttccacac gatgaagtat   1680
aaacagacag acccgaaaca cccggacaac gaccggttca tcctctccag gggacatgct   1740
gctcctatcc tctatgctgc ttgggtggag gtgggtgaca tcagtgaatc tgacttgctg   1800
aacctgagga aacttcacag cgacttggag agacaccctg cccccgattg ccgtttgtt   1860
gacgtggcaa cagggtccct aggtcaggga ttaggtactg catgtggaat ggcttatact   1920
ggcaagtacc ttgacaaggc cagctaccgg gtgttctgcc ttatgggaga tggcgaatcc   1980
tcagaaggct ctgtgtggga ggcttttgct tttgcctccc actacaactt ggacaatctc   2040
gtggcggtct tcgacgtgaa ccgcttggga caaagtggcc ctgcacccct tgagcatggc   2100
gcagacatct accagaattg ctgtgaagcc tttggatgga atacttactt agtggatggc   2160
catgatgtgg aggccttgtg ccaagcattt tggcaagcaa gtcaagtgaa gaacaagcct   2220
actgctatag ttgccaagac cttcaaaggt cgggtattc caaatattga ggatgcagaa   2280
aattggcatg gaaagccagt gccaaaagaa agagcagatg caattgtcaa attaattgag   2340
agtcagatac agaccaatga gaatctcata ccaaaatcgc ctgtggaaga ctcacctcaa   2400
ataagcatca cagatataaa aatgacctcc ccacctgctt acaaagttgg tgacaagata   2460
gctactcaga aaacatatgg tttggctctg gctaaactgg gccgtgcaaa tgaaagagtt   2520
attgttctga gtggtgacac gatgaactcc acctttctg agatattcag gaaagaacac   2580
cctgagcgtt tcatagagtg tattattgct gaacaaaaca tggtaagtgt ggcactaggc   2640
tgtgctacac gtggtcgaac cattgctttt gctggtgctt tgctgccctt ttttactaga   2700
gcattcgatc agctccgaat gggagccatt tctcaagcca atatcaacct tattggttcc   2760
cactgtgggg tatccactgg agaagatgga gtctcccaga tggccctgga ggatctagcc   2820
atgttccgaa gcattcccaa ttgtactgtt ttctatccaa gtgatgccat ctcgacagag   2880
catgctattt atctagccgc caataccaag ggaatgtgct tcattcgaac cagccaacca   2940
gaaactgcag ttatttatac cccacaagaa aattttgaga ttggccaggc caaggtggtc   3000
cgccacggtg tcaatgataa agtcacagta attggagctg gagttactct ccatgaagcc   3060
ttagaagctg ctgaccatct ttctcaacaa ggtatttctg tccgtgtcat cgacccattt   3120
accattaaac ccctggatgc cgccaccatc atctccagtg caaaagccac aggcggccga   3180
gttatcacag tggaggatca ctacaggaa ggtggcattg agaagctgt ttgtgcagct   3240
gtctccaggg agcctgatat ccttgttcat caactggcag tgtcaggagt gcctcaacgt   3300
gggaaaacta gtgaattgct ggatatgttt ggaatcagta ccagacacat tatagcagcc   3360
gtaacactta ctttaatgaa gtaaactagg cttatttcta aaaagtcaag tctattggct   3420
ttggcccaaa agcactggta tctttgtatt aaattcatgt ttattgtcac aaaaccatta   3480
tttataccta tacagttgta ctgtttcttt taaagcaaag ccatttaaca tctttcttca   3540
```

```
<210> SEQ ID NO 2
<211> LENGTH: 625
<212> TYPE: PRT
<213> ORGANISM: Human

<400> SEQUENCE: 2

Met Ala Asn Asp Ala Lys Pro Asp Val Lys Thr Val Gln Val Leu Arg
 1               5                  10                  15

Asp Thr Ala Asn Arg Leu Arg Ile His Ser Ile Arg Ala Thr Cys Ala
                20                  25                  30

Ser Gly Ser Gly Gln Leu Thr Ser Cys Cys Ser Ala Ala Glu Val Val
            35                  40                  45

Ser Val Leu Phe Phe His Thr Met Lys Tyr Lys Gln Thr Asp Pro Glu
    50                  55                  60

His Pro Asp Asn Asp Arg Phe Ile Leu Ser Arg Gly His Ala Ala Pro
65                  70                  75                  80

Ile Leu Tyr Ala Ala Trp Val Glu Val Gly Asp Ile Ser Glu Ser Asp
                85                  90                  95

Leu Leu Asn Leu Arg Lys Leu His Ser Asp Leu Glu Arg His Pro Thr
            100                 105                 110

Pro Arg Leu Pro Phe Val Asp Val Ala Thr Gly Ser Leu Gly Gln Gly
        115                 120                 125

Leu Gly Thr Ala Cys Gly Met Ala Tyr Thr Gly Lys Tyr Leu Asp Lys
    130                 135                 140

Ala Ser Tyr Arg Val Phe Cys Leu Met Gly Asp Gly Glu Ser Ser Glu
145                 150                 155                 160

Gly Ser Val Trp Glu Ala Phe Ala Phe Ala Ser His Tyr Asn Leu Asp
                165                 170                 175

Asn Leu Val Ala Val Phe Asp Val Asn Arg Leu Gly Gln Ser Gly Pro
            180                 185                 190

Ala Pro Leu Glu His Gly Ala Asp Ile Tyr Gln Asn Cys Cys Glu Ala
        195                 200                 205

Phe Gly Trp Asn Thr Tyr Leu Val Asp Gly His Asp Val Glu Ala Leu
    210                 215                 220

Cys Gln Ala Phe Trp Gln Ala Ser Gln Val Lys Asn Lys Pro Thr Ala
225                 230                 235                 240

Ile Val Ala Lys Thr Phe Lys Gly Arg Gly Ile Pro Asn Ile Glu Asp
                245                 250                 255

Ala Glu Asn Trp His Gly Lys Pro Val Pro Lys Glu Arg Ala Asp Ala
            260                 265                 270

Ile Val Lys Leu Ile Glu Ser Gln Ile Gln Thr Asn Glu Asn Leu Ile
        275                 280                 285

Pro Lys Ser Pro Val Glu Asp Ser Pro Gln Ile Ser Ile Thr Asp Ile
    290                 295                 300

Lys Met Thr Ser Pro Pro Ala Tyr Lys Val Gly Asp Lys Ile Ala Thr
305                 310                 315                 320

Gln Lys Thr Tyr Gly Leu Ala Leu Ala Lys Leu Gly Arg Ala Asn Glu
                325                 330                 335

Arg Val Ile Val Leu Ser Gly Asp Thr Met Asn Ser Thr Phe Ser Glu
            340                 345                 350

Ile Phe Arg Lys Glu His Pro Glu Arg Phe Ile Glu Cys Ile Ile Ala
        355                 360                 365

Glu Gln Asn Met Val Ser Val Ala Leu Gly Cys Ala Thr Arg Gly Arg
    370                 375                 380
```

-continued

```
Thr Ile Ala Phe Ala Gly Ala Phe Ala Ala Phe Phe Thr Arg Ala Phe
385                 390                 395                 400

Asp Gln Leu Arg Met Gly Ala Ile Ser Gln Ala Asn Ile Asn Leu Ile
            405                 410                 415

Gly Ser His Cys Gly Val Ser Thr Gly Glu Asp Gly Val Ser Gln Met
        420                 425                 430

Ala Leu Glu Asp Leu Ala Met Phe Arg Ser Ile Pro Asn Cys Thr Val
    435                 440                 445

Phe Tyr Pro Ser Asp Ala Ile Ser Thr Glu His Ala Ile Tyr Leu Ala
450                 455                 460

Ala Asn Thr Lys Gly Met Cys Phe Ile Arg Thr Ser Gln Pro Glu Thr
465                 470                 475                 480

Ala Val Ile Tyr Thr Pro Gln Glu Asn Phe Glu Ile Gly Gln Ala Lys
                485                 490                 495

Val Val Arg His Gly Val Asn Asp Lys Val Thr Val Ile Gly Ala Gly
            500                 505                 510

Val Thr Leu His Glu Ala Leu Glu Ala Ala Asp His Leu Ser Gln Gln
        515                 520                 525

Gly Ile Ser Val Arg Val Ile Asp Pro Phe Thr Ile Lys Pro Leu Asp
    530                 535                 540

Ala Ala Thr Ile Ile Ser Ser Ala Lys Ala Thr Gly Gly Arg Val Ile
545                 550                 555                 560

Thr Val Glu Asp His Tyr Arg Glu Gly Gly Ile Gly Glu Ala Val Cys
                565                 570                 575

Ala Ala Val Ser Arg Glu Pro Asp Ile Leu Val His Gln Leu Ala Val
            580                 585                 590

Ser Gly Val Pro Gln Arg Gly Lys Thr Ser Glu Leu Leu Asp Met Phe
        595                 600                 605

Gly Ile Ser Thr Arg His Ile Ile Ala Ala Val Thr Leu Thr Leu Met
    610                 615                 620

Lys
625

<210> SEQ ID NO 3
<211> LENGTH: 623
<212> TYPE: PRT
<213> ORGANISM: Mouse

<400> SEQUENCE: 3

Met Glu Gly Tyr His Lys Pro Asp Gln Gln Lys Leu Gln Ala Leu Lys
1               5                   10                  15

Asp Thr Ala Asn Arg Leu Arg Ile Ser Ser Ile Gln Ala Thr Thr Ala
            20                  25                  30

Ala Gly Ser Gly His Pro Thr Ser Cys Cys Ser Ala Ala Glu Ile Met
        35                  40                  45

Ala Val Leu Phe Phe His Thr Met Arg Tyr Lys Ala Leu Asp Pro Arg
    50                  55                  60

Asn Pro His Asn Asp Arg Phe Val Leu Ser Lys Gly His Ala Ala Pro
65                  70                  75                  80

Ile Leu Tyr Ala Val Trp Ala Glu Ala Gly Phe Leu Pro Glu Ala Glu
                85                  90                  95

Leu Leu Asn Leu Arg Lys Ile Ser Ser Asp Leu Asp Gly His Pro Val
            100                 105                 110

Pro Lys Gln Ala Phe Thr Asp Val Ala Thr Gly Ser Leu Gly Gln Gly
```

-continued

```
            115                 120                 125
Leu Gly Ala Ala Cys Gly Met Ala Tyr Thr Gly Lys Tyr Phe Asp Lys
        130                 135                 140
Ala Ser Tyr Arg Val Tyr Cys Met Leu Gly Asp Gly Glu Val Ser Glu
145                 150                 155                 160
Gly Ser Val Trp Glu Ala Met Ala Phe Ala Gly Ile Tyr Lys Leu Asp
                165                 170                 175
Asn Leu Val Ala Ile Phe Asp Ile Asn Arg Leu Gly Gln Ser Asp Pro
                180                 185                 190
Ala Pro Leu Gln His Gln Val Asp Ile Tyr Gln Lys Arg Cys Glu Ala
        195                 200                 205
Phe Gly Trp His Thr Ile Ile Val Asp Gly His Ser Val Glu Glu Leu
        210                 215                 220
Cys Lys Ala Phe Gly Gln Ala Lys His Gln Pro Thr Ala Ile Ile Ala
225                 230                 235                 240
Lys Thr Phe Lys Gly Arg Gly Ile Thr Gly Ile Glu Asp Lys Glu Ala
                245                 250                 255
Trp His Gly Lys Pro Leu Pro Lys Asn Met Ala Glu Gln Ile Ile Gln
                260                 265                 270
Glu Ile Tyr Ser Gln Val Gln Ser Lys Lys Ile Leu Ala Thr Pro
        275                 280                 285
Pro Gln Glu Asp Ala Pro Ser Val Asp Ile Ala Asn Ile Arg Met Pro
        290                 295                 300
Thr Pro Pro Ser Tyr Lys Val Gly Asp Lys Ile Ala Thr Arg Lys Ala
305                 310                 315                 320
Tyr Gly Leu Ala Leu Ala Lys Leu Gly His Ala Ser Asp Arg Ile Ile
                325                 330                 335
Ala Leu Asp Gly Asp Thr Lys Asn Ser Thr Phe Ser Glu Leu Phe Lys
                340                 345                 350
Lys Glu His Pro Asp Arg Phe Ile Glu Cys Tyr Ile Ala Glu Gln Asn
        355                 360                 365
Met Val Ser Ile Ala Val Gly Cys Ala Thr Arg Asp Arg Thr Val Pro
        370                 375                 380
Phe Cys Ser Thr Phe Ala Ala Phe Phe Thr Arg Ala Phe Asp Gln Ile
385                 390                 395                 400
Arg Met Ala Ala Ile Ser Glu Ser Asn Ile Asn Leu Cys Gly Ser His
                405                 410                 415
Cys Gly Val Ser Ile Gly Glu Asp Gly Pro Ser Gln Met Ala Leu Glu
                420                 425                 430
Asp Leu Ala Met Phe Arg Ser Val Pro Met Ser Thr Val Phe Tyr Pro
        435                 440                 445
Ser Asp Gly Val Ala Thr Glu Lys Ala Val Glu Leu Ala Ala Asn Thr
450                 455                 460
Lys Gly Ile Cys Phe Ile Arg Thr Ser Arg Pro Glu Asn Ala Ile Ile
465                 470                 475                 480
Tyr Ser Asn Asn Glu Asp Phe Gln Val Gly Gln Ala Lys Val Val Leu
                485                 490                 495
Lys Ser Lys Asp Asp Gln Val Thr Val Ile Gly Ala Gly Val Thr Leu
                500                 505                 510
His Glu Ala Leu Ala Ala Ala Glu Ser Leu Lys Lys Asp Lys Ile Ser
        515                 520                 525
Ile Arg Val Leu Asp Pro Phe Thr Ile Lys Pro Leu Asp Arg Lys Leu
        530                 535                 540
```

-continued

Ile Leu Asp Ser Ala Arg Ala Thr Lys Gly Arg Ile Leu Thr Val Glu
545                 550                 555                 560

Asp His Tyr Tyr Glu Gly Gly Ile Gly Glu Ala Val Ser Ala Val
            565                 570                 575

Val Gly Glu Pro Gly Val Thr Val Thr Arg Leu Ala Val Ser Gln Val
            580                 585                 590

Pro Arg Ser Gly Lys Pro Ala Glu Leu Leu Lys Met Phe Gly Ile Asp
            595                 600                 605

Lys Asp Ala Ile Val Gln Ala Val Lys Gly Leu Val Thr Lys Gly
            610                 615                 620

<210> SEQ ID NO 4
<211> LENGTH: 60
<212> TYPE: PRT
<213> ORGANISM: Yeast

<400> SEQUENCE: 4

Pro His Asn Asp Arg Phe Val Leu Ser Lys Gly His Ala Ala Pro Ile
1               5                   10                  15

Leu Tyr Ala Val Trp Ala Glu Ala Gly Phe Leu Pro Glu Ala Glu Leu
            20                  25                  30

Leu Asn Leu Arg Lys Ile Ser Ser Asp Leu Asp Gly His Pro Val Pro
        35                  40                  45

Lys Gln Ala Phe Thr Asp Val Ala Thr Gly Ser Leu
    50                  55                  60

<210> SEQ ID NO 5
<211> LENGTH: 1284
<212> TYPE: PRT
<213> ORGANISM: Drosophila melanogaster

<400> SEQUENCE: 5

Met Ser Lys Ala Arg Ala Glu Lys Asp Thr Leu Trp Ala Gly Ala Gly
1               5                   10                  15

Val Gly Ala Ala Asp Ala Val Lys Ala Thr Arg Gln Thr Val Asp Ala
            20                  25                  30

Trp Leu Val Ser His Ala Thr Ser Ala Gly Asn Asp Val Val Ser Ser
            35                  40                  45

Thr Ser Pro Thr His Ala Asn Gly Gln Thr Ser Ser Ser Arg Gly Gly
        50                  55                  60

Ser Gly Ala Thr Thr Pro Val Arg Lys Ile Ser Ala His Glu Phe Glu
65                  70                  75                  80

Arg Gly Gly Leu Leu Lys Pro Ile Val Asn Thr Ile Asp Gly Thr Pro
            85                  90                  95

Thr Phe Leu Ser Ile Gly Pro Pro Met Asp Asn Gly Ser Val Gly Gly
            100                 105                 110

Ser Cys Ser Asn Leu Gln Asn Val Gly Val Val Ala Gly Gln Tyr
        115                 120                 125

Gln Tyr Asn His Gln Gln His His Asn His Ala His Leu His His
    130                 135                 140

Ser Gln His Ser His Tyr Gln Ala Gly Ala Val Gly Ser Ser Ser
145                 150                 155                 160

Leu Gly Ser Thr Gly Gly Ala Ser Gly Ala Gly Ala Pro Ser Leu
            165                 170                 175

Gly Gly Ser Gly Gly Ala Gly Asn Gly His Gln Tyr Pro Tyr Tyr His
            180                 185                 190

-continued

```
Cys His Gln Arg Pro Gln Arg Leu Ser Arg Asn Glu Leu Lys Gln Leu
            195                 200                 205

Asp Glu Lys Glu Leu Ile Phe Glu Leu Val Lys Asp Ile Cys Asn Glu
210                 215                 220

Leu Glu Val Arg Thr Leu Cys His Lys Ile Leu Gln Asn Val Ser Ile
225                 230                 235                 240

Leu Leu Asn Ala Asp Arg Gly Ser Leu Phe Leu Val Gln Gly Arg Cys
            245                 250                 255

Asn Gly Pro Asp Gly Leu Lys Lys Cys Leu Val Ser Lys Leu Phe Asp
            260                 265                 270

Val Cys Pro Arg Ser Thr Val Glu Glu Met Glu Gln Gln Asp Glu Val
            275                 280                 285

Arg Val Ala Trp Gly Thr Gly Ile Ala Gly His Val Ala Glu Ser Gly
            290                 295                 300

Glu Pro Val Asn Ile Pro Asp Ala Tyr Gln Asp Glu Arg Phe Asn Cys
305                 310                 315                 320

Glu Ile Asp Ser Leu Thr Gly Tyr Arg Thr Lys Ala Leu Leu Cys Met
            325                 330                 335

Pro Ile Lys Asp Ser Ser Gly Asp Val Ile Gly Val Ala Gln Val Ile
            340                 345                 350

Asn Lys Met Asn Gly Glu Cys Phe Ser Glu Ile Asp Glu Lys Val Phe
            355                 360                 365

Ser Ser Tyr Leu Gln Phe Cys Gly Ile Gly Leu Arg Asn Ala Gln Leu
            370                 375                 380

Tyr Glu Lys Ser Gln Leu Glu Ile Lys Arg Asn Gln Val Leu Leu Asp
385                 390                 395                 400

Leu Ala Arg Met Ile Phe Glu Glu Gln Ser Thr Ile Glu His Met Val
                405                 410                 415

Phe Arg Ile Leu Thr His Met Gln Ser Leu Ile Gln Cys Gln Arg Val
                420                 425                 430

Gln Ile Leu Leu Val His Glu Ala Asp Lys Gly Ser Phe Ser Arg Val
            435                 440                 445

Phe Asp Phe Glu Ala Asn Asp Leu Ser Glu Glu Ala Thr Ser Arg
450                 455                 460

Thr Ser Pro Tyr Glu Ser Arg Phe Pro Ile Asn Ile Gly Ile Thr Gly
465                 470                 475                 480

His Val Ala Thr Thr Gly Glu Thr Val Asn Val Pro Asn Ala Tyr Glu
                485                 490                 495

Asp Asp Arg Phe Asp Ala Ser Val Asp Glu Asn Ser Cys Phe Lys His
            500                 505                 510

Arg Ser Ile Leu Cys Met Ala Ile Lys Asn Ser Leu Gly Gln Ile Ile
            515                 520                 525

Gly Val Ile Gln Leu Ile Asn Lys Phe Asn Glu Leu Asp Phe Thr Lys
            530                 535                 540

Asn Asp Glu Asn Phe Val Glu Ala Phe Ile Phe Cys Gly Met Gly
545                 550                 555                 560

Ile His Asn Thr His Met Tyr Glu Lys Ala Ile Val Ala Met Ala Lys
                565                 570                 575

Gln Ser Val Thr Leu Glu Val Leu Ser Tyr His Ala Ser Ala Thr Met
            580                 585                 590

Asp Glu Ala His Arg Leu Arg Lys Gln Lys Gln Gln Gln Ala Val
            595                 600                 605
```

```
Gly Leu Arg Gln Ala Pro Leu Ser Leu Pro Pro Arg Lys Lys Leu Gln
610                 615                 620

Arg Arg Leu Arg Val Pro Ser Ala Val His Phe Arg Leu His Asp Phe
625                 630                 635                 640

Lys Phe Asp Asp Ile His Phe Glu Asp Asp Thr Leu Lys Ala Cys
                    645                 650                 655

Leu Arg Met Phe Leu Asp Leu Asp Phe Val Glu Arg Phe His Ile Asp
                660                 665                 670

Tyr Glu Val Leu Cys Arg Trp Leu Ser Val Lys Lys Asn Tyr Arg
            675                 680                 685

Asn Val Thr Tyr His Asn Trp Arg His Ala Phe Asn Val Ala Gln Met
    690                 695                 700

Met Phe Ala Ile Leu Thr Thr Thr Gln Trp Trp Lys Ile Phe Gly Glu
705                 710                 715                 720

Ile Glu Cys Leu Ala Leu Ile Ile Gly Cys Leu Cys His Asp Leu Asp
                725                 730                 735

His Arg Gly Thr Asn Asn Ser Phe Gln Ile Lys Ala Ser Ser Pro Leu
            740                 745                 750

Ala Gln Leu Tyr Ser Thr Ser Thr Met Glu His His Phe Asp Gln
            755                 760                 765

Cys Leu Met Ile Leu Asn Ser Pro Gly Asn Gln Ile Leu Ala Asn Leu
770                 775                 780

Ser Ser Asp Asp Tyr Cys Arg Val Ile Arg Val Leu Glu Asp Ala Ile
785                 790                 795                 800

Leu Ser Thr Asp Leu Ala Val Tyr Phe Lys Lys Arg Gly Pro Phe Leu
                805                 810                 815

Glu Ser Val Ser Gln Pro Thr Ser Tyr Trp Val Ala Glu Glu Pro Arg
                820                 825                 830

Ala Leu Leu Arg Ala Met Ser Met Thr Val Cys Asp Leu Ser Ala Ile
            835                 840                 845

Thr Lys Pro Trp Glu Ile Glu Lys Arg Val Ala Asp Leu Val Ser Ser
850                 855                 860

Glu Phe Phe Glu Gln Gly Asp Met Glu Lys Gln Glu Leu Asn Ile Thr
865                 870                 875                 880

Pro Ile Asp Ile Met Asn Arg Glu Lys Glu Asp Glu Leu Pro Met Met
                885                 890                 895

Gln Val Asn Phe Ile Asp Ser Ile Cys Leu Pro Ile Tyr Glu Ala Phe
                900                 905                 910

Ala Thr Leu Ser Asp Lys Leu Glu Pro Leu Val Glu Gly Val Arg Asp
            915                 920                 925

Asn Arg Gly His Trp Ile Asp Leu Ala Asp Val Lys Thr Lys Thr
            930                 935                 940

Ser Gln Asp Gln Glu Pro Glu Glu Gln Gln Gln Asn Val Ile
945                 950                 955                 960

Ser Asn Gly Asp Cys Lys Ala Met Ser Asp Asp Val Ala Ala Ser
                965                 970                 975

Glu Ala Glu Val Ala Val Asp Ser Pro Ser Lys Ala Ser Val Asn
            980                 985                 990

Gly Ser Asn Val Ala Asn Asn Ser Ser Asn Thr Asn Lys Lys Ile Ala
            995                 1000                1005

Val Ala Ser His Pro Thr Ser Thr Gln Pro Ser Asp Asp Asn Asp
    1010                1015                1020

Val Asp Ala Asp Ala Asp Asp Val Asp Glu Gln Ala Ala Glu Glu Asn
```

-continued

```
                  1025                1030                1035                1040
Gly His Asp Ala Glu Val Asp Glu Ala Ser Cys Arg Ser Asn Ser Thr
                  1045                1050                1055
Cys Ser Ser Ser Thr Ala Ser Ser Cys Leu Ser Thr Pro Pro Pro Thr
                  1060                1065                1070
Gly Glu Asp Asp Ser Thr Pro Val Ser Pro Leu Lys Thr Leu Gln Ala
                  1075                1080                1085
Lys Leu Val Ala Ala Asn Leu Asn Ala Leu Gln Arg Gln Thr Ser Asn
                  1090                1095                1100
Gln Ala Gln Thr Gln Lys Gln Arg Cys Lys Ser Cys Asp His Ser Arg
1105                1110                1115                1120
Ser Gly Leu Gln Val Arg Lys Thr Ser Ser Leu Arg Gly Ala Gln Glu
                  1125                1130                1135
Leu Asp Leu Asp Ser Lys Thr Arg Asn Gly Thr His Ala Ala Leu Cys
                  1140                1145                1150
Lys Ser Thr Pro Val Ile Asn Asn His Ser His His Asn His Ser
                  1155                1160                1165
His Ser His Asn His Asn His His His His His His His Ser His
                  1170                1175                1180
His Asn His Ser Gln His Gly Ile Gly Ile Gly Ser Ala Ser Ile Gly
1185                1190                1195                1200
Gly Ser Gly Leu Ile Ser Leu Thr Thr Pro Leu Leu Ala Met Asp Ser
                  1205                1210                1215
Asp Arg Ile Pro Lys Ile Val Gly Lys Ile Gly Asn Leu Asp Gly Leu
                  1220                1225                1230
Pro Phe Ala Asn Gly Ile Gly Gly Pro Gln Asn Gly His Gly Leu Pro
                  1235                1240                1245
Phe Gly Ser Tyr Gln His His His His Gln His His His Leu
                  1250                1255                1260
Leu Ala Arg Arg His Ser Glu Thr Asn Ser Asn Gly Ala Thr Ala Met
1265                1270                1275                1280
Ala Val Glu Lys

<210> SEQ ID NO 6
<211> LENGTH: 1881
<212> TYPE: DNA
<213> ORGANISM: Human

<400> SEQUENCE: 6
atgatggcca acgacgccaa gcccgacgtg aagaccgtgc aggtgctgcg ggacacagcc      60
aaccgcctgc ggatccattc catcagggcc acgtgtgcct ctggttctgg ccagctcacg     120
tcgtgctgca gtgcagcgga ggtcgtgtct gtcctcttct tccacacgat gaagtataaa     180
cagacagacc cagaacaccc ggacaacgac cggttcatcc tctccagggg acatgctgct     240
cctatcctct atgctgcttg ggtggaggtg ggtgacatca gtgaatctga cttgctgaac     300
ctgaggaaac ttcacagcga cttggagaga caccctaccc cccgattgcc gtttgttgac     360
gtggcaacag ggtccctagg tcagggatta ggtactgcat gtggaatggc ttatactggc     420
aagtaccttg acaaggccag ctaccgggtg ttctgcctta tgggagatgg cgaatcctca     480
gaaggctctg tgtgggaggc ttttgctttt gcctcccact acaacttgga caatctcgtg     540
gcggtcttcg acgtgaaccg cttgggacaa gtggccctg caccccttga gcatggcgca     600
gacatctacc agaattgctg tgaagccttt ggatggaata cttacttagt ggatggccat     660
```

-continued

```
gatgtggagg ccttgtgcca agcattttgg caagcaagtc aagtgaagaa caagcctact     720
gctatagttg ccaagacctt caaaggtcgg ggtattccaa atattgagga tgcagaaaat     780
tggcatggaa agccagtgcc aaaagaaaga gcagatgcaa ttgtcaaatt aattgagagt     840
cagatacaga ccaatgagaa tctcatacca aaatcgcctg tggaagactc acctcaaata     900
agcatcacag atataaaaat gacctcccca cctgcttaca aagttggtga caagatagct     960
actcagaaaa catatggttt ggctctggct aaactgggcc gtgcaaatga aagagttatt    1020
gttctgagtg gtgacacgat gaactccacc ttttctgaga tattcaggaa agaacaccct    1080
gagcgtttca tagagtgtat tattgctgaa caaaacatgg taagtgtggc actaggctgt    1140
gctacacgtg gtcgaaccat tgcttttgct ggtgcttttg ctgccttttt tactagagca    1200
ttcgatcagc tccgaatggg agccatttct caagccaata tcaaccttat tggttcccac    1260
tgtggggtat ccactggaga agatggagtc tcccagatgg ccctggagga tctagccatg    1320
ttccgaagca ttcccaattg tactgttttc tatccaagtg atgccatctc gacagagcat    1380
gctatttatc tagccgccaa taccaaggga atgtgcttca ttcgaaccag ccaaccagaa    1440
actgcagtta tttatacccc acaagaaaat tttgagattg gccaggccaa ggtggtccgc    1500
cacggtgtca atgataaagt cacagtaatt ggagctggag ttactctcca tgaagcctta    1560
gaagctgctg accatctttc tcaacaaggt atttctgtcc gtgtcatcga cccatttacc    1620
attaaacccc tggatgccgc caccatcatc tccagtgcaa aagccacagg cggccgagtt    1680
atcacagtgg aggatcacta cagggaaggt ggcattggag aagctgtttg tgcagctgtc    1740
tccagggagc ctgatatcct tgttcatcaa ctggcagtgt caggagtgcc tcaacgtggg    1800
aaaactagtg aattgctgga tatgtttgga atcagtacca gacacattat agcagccgta    1860
acacttactt taatgaagta a                                              1881
```